United States Patent [19]
Chupp et al.

[11] Patent Number: 4,467,125
[45] Date of Patent: Aug. 21, 1984

[54] NITRO-METHYL OR ETHYL SUBSTITUTED BENZOTRIFLUORIDE

[75] Inventors: John P. Chupp, Kirkwood; Gerhard H. Alt, University City, both of Mo.

[73] Assignee: Monsanto Company, St. Louis, Mo.

[21] Appl. No.: 503,375

[22] Filed: Jun. 10, 1983

[51] Int. Cl.³ ............................................. C07C 79/12
[52] U.S. Cl. ...................................... 568/936; 564/305
[58] Field of Search .......................................... 568/936

[56] References Cited
U.S. PATENT DOCUMENTS 4,242,286 12/1980 Ohsaka ............................ 568/936 X
4,393,257 7/1983 Nakagawa et al. ............. 568/936 X

FOREIGN PATENT DOCUMENTS 2750170 5/1978 Fed. Rep. of Germany .

OTHER PUBLICATIONS

Roberts et al., J. Am. Chem. Soc., vol. 72, pp. 408 to 410, (1950).

Primary Examiner—Leland A. Sebastian
Attorney, Agent, or Firm—Robert B. Martin; Richard H. Shear

[57] ABSTRACT

The invention herein pertains to nitro-methyl or ethyl substituted benzotrifluoride compounds useful as chemical intermediates and a process for their preparation. The chemical intermediates are useful for the preparation of substituted anilines which are precursors for a new class of 2-haloacetanilide herbicides.

10 Claims, No Drawings

4,467,125

NITRO-METHYL OR ETHYL SUBSTITUTED BENZOTRIFLUORIDE

FIELD OF THE INVENTION

The invention herein pertains to nitrosubstituted benzotrifluoride compounds as chemical intermediates and a process for their preparation. The chemical intermediates are useful for the preparation of substituted anilines which are precursors for a new class of 2-haloacetanilide herbicides.

BACKGROUND OF THE INVENTION

It has recently been discovered that a certain class of 2-haloacetanilide herbicides are particularly useful in safely controlling hard-to-kill perennial weeds, such as quackgrass, nutsedges and many others in the presence of a variety of crops including cotton, corn, and soybean. This new class of herbicides is described and claimed in Brazilian Pat. No. 887,997 issued Sept. 18, 1981. Two particularly effective herbicides within this class are N-(ethoxymethyl)-2'-trifluoromethyl-6'-methyl-2-chloroacetanilide and N-(ethoxymethyl)-2'-trifluoromethyl-6'-ethyl-2-chloroacetanilide.

The present invention relates to two intermediates in the production of compounds within this new class of herbicides. The present invention also relates to a process for preparing these two intermediates. This process generally involves nitration of a substituted benzotrifluoride compound.

Electrophilic substitution, such as nitration, halogenation, sulfonation, etc. of substituted benzene compounds is known in the art. It is also known that substituents on the benzene ring can affect both the reactivity and orientation of electrophilic substitution. Certain substituents can increase the reactivity of the benzene ring by donating electron density to the ring inductively or by resonance. Other groups withdraw electron density from the ring and thus reduce the reactivity of the ring.

Ring substituents can either direct electrophilic substitution at the ortho, para, or meta positions. With disubstituted benzene compounds, the two substituents can either reinforce or oppose each others directive influence. Activating substituents generally prevail over deactivating substituents. However, because of the sensitivity of electrophilic substitution to steric hindrance, there normally is little substitution between two substituents meta to each other regardless of the directive effect of the ring substituents. For example, nitration of meta-chloro-toluene results in only about 9% 2-nitro-3-chloro-toluene and about 59% 6-nitro-3-chloro-toluene. Nitration of 3-chloro benzoic acid results in only about 8% of the 2-nitro-3-chlorobenzoic acid.

It is known that a few specific meta-disubstituted benzene compounds direct a significant portion of electrophilic substitution between the two substituents. These specific compounds have an ortho-para directing substituent and a meta-directing substituent having an $sp^2$ carbon atom bonded to the ring. Tomisek discloses that nitration of meta-toluic acid results in about 48% yield of the 2-nitro-3-toluic acid. (JACS 1588 (1946)) Hodgson discloses that nitration of 3-methoxybenzaldehyde results in about 56% yield of 2-nitro-3-methoxybenzaldehyde. (Aromatic Substitution Nitration and Halogenation by DeLa Mare & Ridd (1959)) However, Hodgson also discloses that nitration of the 3-hydroxybenzaldehyde which has an ortho-para directing substituent and a meta-directing substituent with an $sp^2$ carbon atom bonded to the ring results in only about 3.5% yield of the 2-nitro-3-hydroxybenzaldehyde. Elliott predicts the orientation of aromatic substitution in a number of substituted benzene compound from M.O. calculations and predicts the nitration of 3-methyl benzotrifluoride in the 2 and 6 positions. Theochem 3 (4) 301 (1982). However, Elliott does not predict the 2 isomer as the major isomer.

It is an object of the present invention to provide new intermediate compounds useful in the production of compounds within a new class of 2-haloacetanilide herbicides.

It is another object of this invention to provide a process for producing these new intermediate compounds.

It is another object of this invention to provide a new aromatic nitration directing system.

Other objects and advantages will become apparent from the following disclosure.

SUMMARY OF THE INVENTION

The present invention relates to two intermediate compounds and a process for making the compounds. The compounds are intermediates in the production of substituted anilines which are precursors for the preparation of compounds within a new class of 2-haloacetanilide herbicides.

The novel intermediate compounds of this invention are 2-nitro-3-methyl benzotrifluoride and 2-nitro-3-ethyl benzotrifluoride.

The process of the present invention for making the novel nitro-substituted benzotrifluoride compounds generally involves nitrating the corresponding alkyl-substituted benzotrifluoride compound with nitric acid at lower temperatures. The nitration of the corresponding benzotrifluoride compound having a meta-directing substituent with an $sp^3$ carbon atom results in the formation of an unexpectedly large amount of 2-nitro isomer. The nitration also results in the formation of the 4-nitro and 6-nitro isomers. The 2-nitro-3-alkyl benzotrifluoride intermediates of the present invention may be separated from the other nitrated products by distillation.

The novel intermediate compounds of the present invention may be converted into corresponding anilines which are precursors for compounds within the new class of 2-haloacetanilide herbicides. The intermediate compound can be hydrogenated following standard laboratory procedures to form the precursor aniline. The precursor aniline can then be converted into compounds within the new class of herbicides according to known procedures. A more thorough disclosure of the present invention is presented in the detailed description which follows.

DETAILED DESCRIPTION OF THE INVENTION

The present invention relates to two intermediate compounds and the process for making these intermediate compounds.

The novel intermediate compounds of the present invention are: (a) 2-nitro-3-methyl benzotrifluoride (1-trifluoromethyl-2-nitro-3-methyl benzene) and (b) 2-nitro-3-ethyl benzotrifluoride (1-trifluoro-2-nitro-3-ethyl benzene). The compounds have the following formula:

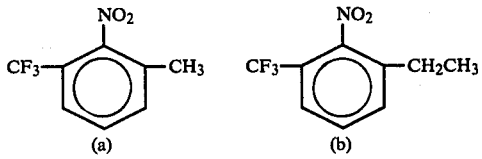

(a)    (b)

The process of the present invention for making the novel intermediates generally involves nitrating the corresponding alkyl-substituted benzotrifluoride compound with nitric acid at lower temperatures. The starting 3-methyl benzotrifluoride can be made by reacting the Grignard reagent of m-trifluoromethyl phenyl magnesium with dimethyl sulfate by procedures set forth in J.A.C.S. 65 389 (1943). The 3-methyl benzotrifluoride can also be prepared by reacting m-iodotoluene with the sodium salt of trifluoroacetic acid and copper iodide. (Chem Letters 1719, 1981). The starting 3-ethyl benzotrifluoride can be prepared by reduction of commercially available m-trifluoromethyl acetophenone by known laboratory methods. Other methods of preparing 3-ethyl benzotrifluoride will be obvious to those skilled in the art.

The 3-alkyl benzotrifluoride is then nitrated with a suitable nitrating agent such as nitric acid, oxides of nitrogen, e.g. dinitrogen pentoxide, or nitronium tetrafluoroborate. The nitration reaction can be conveniently accomplished using nitric acid. Conveniently the nitration uses a molar excess of nitric acid from about three to ten molar equivalents, e.g. about three to ten moles of nitric acid per mole of benzotrifluoride. Conveniently, the nitric acid has a concentration of 80% or greater, preferably about 98% nitric acid. The nitric acid may also be fuming nitric acid. The molar excess of nitric acid functions to maintain a concentrated solution of the acid during the course of the reaction thereby maintaining a convenient reaction rate. Other acids may be used as a cosolvent to maintain a concentrated acid solution, such as sulfuric acid or hydrofluroic acid. However, it has been found that the presence of sulfuric acid may, in some cases, result in the formation of greater amounts of the 4- and 6-nitro isomers as nitration products. Conveniently the nitration reaction is run at a temperature from about −40° C. to about 50° C. and preferably about −20° C. to about 10° C. It has been found that, in some cases, higher temperatures may result in the formation of smaller amounts of the 2-nitro isomer.

Normally the reaction is run without the use of any solvents. However, in some cases, it may be desired to use an inert solvent to moderate the temperature of the exothermic nitration reaction. Solvents may also be useful in the separation of the reaction products. Suitable inert organic solvents which may be used are methylene chloride, nitromethane, carbon tetrachloride, sulfolane, and ethylene dichloride. It will be obvious to one skilled in the art that other solvents may also be useful in the practice of the present invention.

Conveniently the reaction vessel is first charged with a suitable amount of concentrated nitric acid, e.g. three to five molar equivalents. Preferably the corresponding alkyl-substituted benzotrifluoride is then added slowly with vigorous stirring to the nitric acid with external cooling to maintain the reaction temperature within the preferred range. After completion of the addition, the reaction mixture is stirred for a short period of time of about one hour to ensure that the nitration reaction is complete.

The mononitration reaction results in the formation of the 2-nitro, 4-nitro, and 6-nitro isomers plus trace amounts of the 5-nitro isomer and other reacted and unreacted by-products. After the mononitration reaction is completed, the nitration products are separated from the reaction medium. Conveniently, the reaction mixture can be added to ice water and the nitration products separated from the aqueous acid solution by phase separation optionally with the addition of a suitable organic solvent, such as methylene chloride. The organic layer is then washed with a basic solution, such as aqueous sodium bicarbonate or sodium hydroxide, to remove any residual spent acid and traces of aromatic carboxylic acids.

In commercial applications, the nitric acid may be separated from the organic products using extractive solvents and/or minimal water. The nitric acid could then be dehydrated and recycled.

The 2-nitro isomer may then be separated from the other nitration products by any suitable means such as fractional distillation, chromatography or other methods known to those skilled in the art. One suitable method for separating the 2-nitro isomer from the 4-nitro and 6-nitro isomers is fractional distillation. It has been demonstrated that a column having about 20 theoretical plates and a reflux ratio of 4:1 can separate off about 50% of the 2-nitro-3-methyl benzotrifluoride isomer at about 98% purity. It will be obvious to one skilled in the art that a greater amount of the 2-nitro isomer can be recovered using other distillation columns.

The isolated 2-nitro isomer may then be reduced to form the corresponding aniline which is a precursor material for compounds within the new class of 2-haloacetanilide herbicides. The precursor aniline may be formed by hydrogenating the 2-nitro isomer. Conveniently, the 2-nitro isomer is dissolved in a suitable solvent. Among the wide variety of suitable solvents for this process are various polar solvents including alcohols, ethers, hydrocarbons, water and the like. Preferred are alcohols, such as methanol or ethanol optionally aqueous.

The reaction mixture also conveniently includes a hydrogenation catalyst. Suitable hydrogenation catalysts are metal catalysts such as palladium, platinum, rhodium, nickel and the like, which most often are available on porous supports. Palladium on carbon catalysts are commercially available in concentrations of 1% to 10% palladium. The supported catalysts are generally present in amounts less than 10% by weight of the reaction mixture.

The above-described reagents are conveniently combined in a suitable vessel equipped with means for stirring and introducing gaseous hydrogen. The hydrogenation reaction can be carried out at any suitable hydrogen pressure from atmospheric to about 61 atmospheres. Preferred are hydrogen pressures of from about 3.4–13.6 atms. After the pressure drop indicates completion of the reaction, the reaction mixture is filtered, washed, dried, and stripped of solvent to give the precursor aniline product.

The precursor aniline may then be converted to the compounds within the new class of 2-haloacetanilide by a variety of methods. For example, tertiary 2-haloacetanilide may be prepared by haloacetylation of the precursor aniline by known procedures to form a secondary 2-haloacetanilide which is then N-alkylated to form compounds within the new class of 2-haloacetanilide herbicides. The haloacetylation of the aniline can be accomplished by adding a slight molar excess of chloroacetyl chloride to the aniline in a suitable organic solvent, such as chlorobenzene, and heating the solution to reflux for a short period of time. The secondary 2-haloacetanilide is then N-alkylated according to known procedures.

An N-alkylation process is described in detail in U.S. Pat. No. 4,258,196. A modified N-alkylation process is described in U.S. Pat. No. 4,284,564. The 2-haloacetanilides may also be made by a transetherification process. This process is described in U.S. Pat. No. 4,296,254. Tertiary 2-haloacetanilides may also be prepared from the precursor aniline in accordance with the procedures disclosed in Brazilian Pat. No. 887,997. These patents are incorporated herein by reference.

An alternative method of obtaining the precursor aniline of the corresponding 2-nitro isomer involves a modification of the separation and reduction steps. The crude reaction mixture containing the 2-, 4-, and 6-nitro isomers may be fractionally distilled to separate the 2- and 4-nitro isomers from the 6-nitro isomer. The recovered 2- and 4-nitro isomers may then be hydrogenated according to the above-described procedure to form the corresponding anilines. The 2-amino-3-alkyl benzotrifluoride can then be fractionally distilled from the mixture of 2-amino-3-methyl benzotrifluoride and 4-amino-3-methyl benzotrifluoride.

The following examples are presented to illustrate the present invention as well as some of the various embodiments of the invention. These examples are presented as being illustrative of the novel process of the invention and are not intended to be a limitation as to the scope thereof.

EXAMPLE I

2-Nitro-3-Methyl Benzotrifluoride

The nitration vessel is charged with 250 gms (3.97 moles) of 98% $HNO_3$ and cooled to about $-18°$ C. Then 100 gms (0.62 moles) of 3-methyl benzotrifluoride is added dropwise with stirring and the temperature is maintained within the range of about $-16°$ C. to about $-22°$ C. The addition of the benzotrifluoride takes about 2 hours and 15 minutes. After it has been added, stirring is continued for about another 15 minutes. The reaction mixture is poured into ice water and methylene chloride is added to phase separate the nitration products. The organic layer is washed with sodium carbonate solution. The solvent is then stripped on a rotary evaporator. Yield is 127.5 gms of oil comprising 43% 2-nitro isomer; 31% 4-nitro isomer, 24% 6-nitro isomer and about 1% of the 5-nitro isomer as determined by glc and $^{19}F$ NMR.

EXAMPLE II

2-Nitro-3-Methyl Benzotrifluoride

Following the same procedures and reactant charges as given in Example I, the nitration was carried out at $-30°$ C. to $-31°$ C., with 2 hours and 15 minutes addition time and three-quarters of an hour stirring period. The reaction mixture was treated with ice and water (about 1 kg), extracted with methylene chloride, vacuum stripped of solvent, and filtered through clay. Yield 127.4 gms of yellow oil. Isomer distribution by $^{19}F$ NMR:

46.6%; 26.5%; 26.9% of 2-, 6- and 4-nitro isomer; by $^1H$ NMR:

45.7%; 27.8%; 26.6% of 2-, 6- and 4-nitro isomers.

EXAMPLE III

2-Nitro-3-Methyl Benzotrifluoride 2 gms of 3-methyl benzotrifluoride is dissolved in 5 mls of methylene chloride and added dropwise with stirring at $-20°$ C. to $-25°$ C. to 6 gms of 98% $HNO_3$ dissolved in 10 ml methylene chloride. After addition, the reaction was allowed to finish by warming the mixture to 15° C. After treatment with ice and water followed by sodium bicarbonate wash, near quantitative yield was recovered. Isomer distribution was as follows:

44%; 29%; 26.6% as 2-, 6- and 4-nitro isomers.

EXAMPLE IV

2-Nitro-3-Methyl Benzotrifluoride 6 gms of 90% nitric acid is cooled to $-5°$ C. and 2 gms of 3-methyl benzotrifluoride was added dropwise with stirring. The two phase system was allowed to warm to 10° C. during addition. After stirring 2 hours, the reaction mixture was poured onto ice, extracted with methylene chloride and washed with dilute aqueous sodium bicarbonate. After vacuum removal of solvent on a rotary evaporator, near quantitative oil was obtained which had isomer distribution:

44.2%; 31.1%; 24.5% as 2-, 6- and 4-nitro isomers, respectively.

EXAMPLE V

2-Nitro-3-Ethyl Benzotrifluoride 3.1 gms of 3-ethyl benzotrifluoride is added slowly over a period of one half hour to 8 gms of 98% $HNO_3$ at $-10°$ C. After addition, the mixture is heated to 10° C. and poured into ice. The organic layer is separated, washed with $NaHCO_3$ and treated with 50 ml of $CH_2Cl_2$. $CH_2Cl_2$ is vacuum distilled. Recovered near quantitative yield of an amber-colored oil. $^{19}F$ NMR and gc 6, 2 and 4 isomer ratio as:

43.83; 34.2; and 20.1, respectively.

EXAMPLE VI

Distillation of Isomer Mixture 317 gms (1.55 moles) of mononitrated 3-methyl benzotrifluoride containing about 145 gms, 89 gms, and 79 gms of the 2-, 4- and 6-nitro isomers, respectively, is charged to an Oldershaw column with 30 trays (about 20 theoretical plates) and an adjusted reflux ratio 4:1. Nine fractions were taken from 77.5° C. to 85° C. at 4.6 mm to 4.8 mm pressure. The fractions 1–7 weighed a total of 145.3 gms and contained 41% of the original charged 2-nitro isomer while fraction 8, bp. 82–84 (4.6 mm) weighed 74.1 gms at 98.4% assay of 2-nitro represented 51% of the charged 2 isomer. The fractions 6–9 contained less than 1% of the 6-nitro isomer. The high assay (about 98% purity) of 2-nitro isomer separated as described above in a low melting colorless to light yellow oil that crystallizes readily on standing. It can be recrystallized from cold methanol as colorless crystals with mp. of 31°–32° C. $^1H$ NMR ($CDCl_3$ with tetramethyl silane as internal standard) γ 2.18 (S, 3H, $ArCH_3$), 7.29 (S, 3H, ArH).

|  | C | H | N |
|---|---|---|---|
| Calculated for $C_8H_6F_3NO_2$: | 46.84 | 2.95 | 6.83 |
| Found: | 46.78 | 2.98 | 6.82 |

EXAMPLE VII

2-Amino-3-Methyl Benzotrifluoride 139.4 gms (0.68 moles) of a mixture of 2- and 4-nitro 3-methyl benzotrifluoride plus some impurities were charged to autoclave with 400 ml methyl alcohol and 1.0 gms 5% Pd/C catalyst. The clave was pressurized to 54.4 atms with $H_2$ and heated with stirring to 50° C. whereupon facile hydrogenation took place. After a pressure drop to 13.6 atms occurred, clave was repressured again to 54.4 atms and allowed to fall again to 12.25 atms. Upon cooling the clave was vented, contents filtered through Celite, taken up in 100 ml $CH_2Cl_2$ and washed successively with 250 ml sat. NaCl, followed by a water wash. The water washes extracted twice the 75 ml portions each of $CH_2Cl_2$. The solution was dried over $MgSO_4$, filtered, then stripped cold to give 116.6 gms (98%) yield of 2- and 4-amino isomers of 3-methyl benzotrifluoride.

EXAMPLE VIII

2-Amino-3-Methyl Benzotrifluoride 178 gms of 2- and 4-amino-3-methyl benzotrifluoride (about 61–64% of 2-isomer) is charged into a 30 tray Oldershaw column with reflux ratio of 4:1. The first three fractions taken between 64° C. and 68° C. (5.3 mm) weighed 107.2 gms and consisted of 94% of the charged 2-amino isomer (99.3% assay). The fourth fraction taken between 72° C. and 78° C. (5.5 mm) weighed 7.2 gms. The purified 2-amino 3-methyl benzotrifluoride is originally a colorless oil, which like most anilines, darkens on standing. ND 1.4820; 'H NMR (CDCl₃ with tetramethylsilane as internal standard), F 2.11, s, 3H, ArCH₃, 4.05 (broad, 2, NH₂), multiplets centered at 6.6 and 7.2 (3, ArH).

|  | C | H | N |
|---|---|---|---|
| Calculated for $C_8H_8F_3N$: | 54.86 | 4.60 | 8.00 |
| Found: | 55.25 | 4.65 | 8.02 |

Although this invention has been described with respect to specific embodiments, the details thereof are not to be construed as limitations, for it will be apparent that various embodiments, changes and modifications may be resorted to without departing from the spirit and scope thereof and it is understood that such equivalent embodiments are intended to be included within the scope of this invention.

We claim:

1. A compound having the formula:

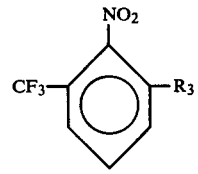

wherein the above formula R is methyl or ethyl.

2. The compound of claim 1 wherein R is methyl.

3. The compound of claim 1 wherein R is ethyl.

4. A process for preparing a compound having the formula:

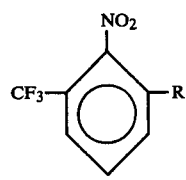

which comprises nitrating the compound having the formula:

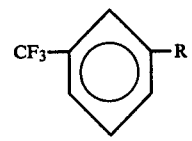

wherein the above formulae R is methyl or ethyl.

5. The process of claim 4 wherein R is methyl.

6. The process of claim 4 wherein R is ethyl.

7. The process of claim 4 wherein the compound of formula II is nitrated with about three to about ten molar equivalents of concentrated nitric acid.

8. The process of claim 4 wherein said nitration is carried out at a temperature of about −40° C. to about 50° C.

9. The process of claim 4 wherein said nitration is carried out at a temperature from about −20° C. to about 10° C.

10. The process of claim 4 wherein said process further includes the step of separating the 2-nitro isomer from the reaction medium by distillation.

* * * * *